United States Patent
Russell (10) Patent No.: US 9,201,002 B2
(45) Date of Patent: Dec. 1, 2015

(54) GAS MEASUREMENT MODULE FOR USE IN THERAPEUTIC SETTINGS HAVING A MICROSPECTROMETER WITH A SHORTENED OPTICAL PATH

(75) Inventor: James T. Russell, Bellevue, WA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 361 days.

(21) Appl. No.: 13/519,027

(22) PCT Filed: Dec. 27, 2010

(86) PCT No.: PCT/IB2010/056085
§ 371 (c)(1),
(2), (4) Date: Jun. 25, 2012

(87) PCT Pub. No.: WO2011/080694
PCT Pub. Date: Jul. 7, 2011

(65) Prior Publication Data
US 2013/0119254 A1    May 16, 2013

Related U.S. Application Data (60) Provisional application No. 61/290,556, filed on Dec. 29, 2009.

(51) Int. Cl.
*G01N 21/35* (2014.01)
*A61B 5/083* (2006.01)
*G01N 21/3504* (2014.01)

(52) U.S. Cl.
CPC .............. *G01N 21/35* (2013.01); *A61B 5/0836* (2013.01); *G01N 21/3504* (2013.01)

(58) Field of Classification Search
CPC . G01N 21/3504; G01N 21/35; A61B 5/0836; B24B 37/26; B24D 11/00; B24D 13/147; B24D 2203/00
USPC .......................... 250/339.07, 339.01, 339.06
See application file for complete search history.

(56) References Cited

U.S. PATENT DOCUMENTS

| | | |
|---|---|---|
| 4,423,739 A | 1/1984 | Passaro |
| 6,943,885 B2 | 9/2005 | Martin |
| 6,981,947 B2* | 1/2006 | Melker ........................ 600/532 |
| 7,605,370 B2 | 10/2009 | Russell |
| 2006/0064255 A1 | 3/2006 | Johnson |
| 2010/0110447 A1* | 5/2010 | Cox et al. ...................... 356/519 |

FOREIGN PATENT DOCUMENTS

| | | |
|---|---|---|
| CN | 101248336 A | 8/2008 |
| EP | 2065697 A1 | 6/2009 |

(Continued)

*Primary Examiner* — Mark R Gaworecki
(74) *Attorney, Agent, or Firm* — Randall M. Berman (57) ABSTRACT

Gas within a ventilation circuit (12) is analyzed by a spectrometer included in gas measurement module (16) that is inserted into the respiratory circuit. The gas measurement module includes an infrared source and a movable filter member comprising at least two filter elements. The optical path length of the spectrometer is reduced. This includes removing optical components configured to collimate or focus electromagnetic radiation within the spectrometer. However, path length of the spectrometer is reduced to the point that other enhancements associated with path length reduction outweigh losses to precision and/or accuracy caused by beam expansion in the spectrometer.

15 Claims, 6 Drawing Sheets

(56) References Cited

FOREIGN PATENT DOCUMENTS

| JP | 2228943 | A | 9/1990 |
|----|---------|----|--------|
| JP | 523343 | B2 | 9/1993 |
| JP | 9089765 | A | 4/1997 |
| JP | 200549279 | A | 2/2005 |
| JP | 200591003 | A | 4/2005 |
| JP | 2007236733 | A | 9/2007 |
| JP | 2008157634 | A | 7/2008 |
| WO | 2011070485 | A1 | 6/2011 |

* cited by examiner

GAS MEASUREMENT MODULE FOR USE IN THERAPEUTIC SETTINGS HAVING A MICROSPECTROMETER WITH A SHORTENED OPTICAL PATH

BACKGROUND OF THE INVENTION

1. Field of the Invention

The invention relates to a gas measurement module that is insertable into a respiratory circuit, and carries a microspectrometer configured to detect gas composition within the respiratory circuit.

2. Description of the Related Art

Gas analyzers are widely used in medical applications and may be characterized as being located either in the main path of the patient's respiratory gases (mainstream analyzers) or in an ancillary path usually paralleling the main path (sidestream analyzers). A mainstream analyzer is situated such that the subject's inspired and expired respiratory gases pass through an airway adapter onto which the analyzer is placed. A sidestream gas analyzer is coupled to an airway adapter to draw air off from the main respiratory circuit for measurement. Mainstream and sidestream designs for inclusion in gas measurement modules that can be coupled to a respiratory circuit in a therapeutic setting to measure gas composition must be designed to facilitate installation of the gas measurement modules at a patient's airway or in a respiratory circuit in communication with a patient in a location in relatively close proximity to the patient. As a result, to be accepted in therapeutic settings, the gas analyzer must be designed such that the gas measurement module housing the gas analyzer has a convenient and comfortable form factor and/or weight. Further, the gas analyzer must be robust enough to be substantially unaffected by typical mechanical abuse and temperature variations associated with use in therapeutic settings.

SUMMARY OF THE INVENTION

One aspect of the invention relates to a gas measurement module configured to be inserted into a respiratory circuit that is in fluid communication with an airway of a subject. The gas measurement module comprises a chamber, an infrared source, a movable filter member, a photosensitive detector, and an actuator. The chamber has a first opening and a second opening. The chamber is configured to form a flow path between the first opening and the second opening such that if the gas measurement module is inserted into the respiratory circuit, gas from the airway of the subject is transported through the flow path. The infrared source is configured to emit infrared electromagnetic radiation along an optical path that passes through the flow path formed by the chamber. The movable filter member includes a first filter element configured to filter electromagnetic radiation in a first wavelength band, and a second filter element configured to filter electromagnetic radiation in a second wavelength band. The photosensitive detector is held at a fixed position along the optical path to receive infrared electromagnetic radiation that has been filtered by the filter member and has passed through the flow path formed by the chamber. The photosensitive detector is configured to generate output signals that convey information related to one or more parameters of the received infrared electromagnetic radiation. The actuator is configured to actuate the filter member between a first position and a second position, wherein at the first position the first filter element is positioned in the optical path, and wherein at the second position the second filter element is positioned in the optical path.

Another aspect of the invention relates to a method of analyzing gas within a gas measurement module configured to be inserted into a respiratory circuit that is in fluid communication with an airway of a subject. In one embodiment, the method comprises emitting infrared electromagnetic radiation along an optical path that passes through a flow path formed by the gas measurement module within which gas from the airway of the subject flows; actuating a filter member between a first position and a second position, wherein at the first position a first filter element of the filter member is disposed in the optical path and at the second position a second filter element of the filter member is disposed in the optical path, and wherein the first filter element is configured to filter electromagnetic radiation in a first wavelength range and the second filter element is configured to filter electromagnetic radiation in a second wavelength range; receiving electromagnetic radiation along the optical path that has been filtered by the filter member; and generating output signals that convey information related to one or more parameters of the received infrared electromagnetic radiation.

Yet another aspect of the invention relates to a system configured to analyze gas, wherein the system configured to be inserted into a respiratory circuit that is in fluid communication with an airway of a subject. In one embodiment, the system comprises means for emitting infrared electromagnetic radiation along an optical path that passes through a flow path within which gas from the airway of the subject flows; means for filtering electromagnetic radiation disposed along the optical path, wherein the means for filtering comprise first means for filtering electromagnetic radiation in a first wavelength range and second means for filtering electromagnetic radiation in a second wavelength range; means for actuating the means for filtering between a first position and a second position, wherein at the first position the first means for filtering filter electromagnetic radiation traveling along the optical path and at the second position the second means for filtering filter electromagnetic radiation traveling along the optical path; means for receiving electromagnetic radiation along the optical path that has been filtered by the filter member and generating output signals that convey information related to one or more parameters of the received infrared electromagnetic radiation.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn in proportion. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
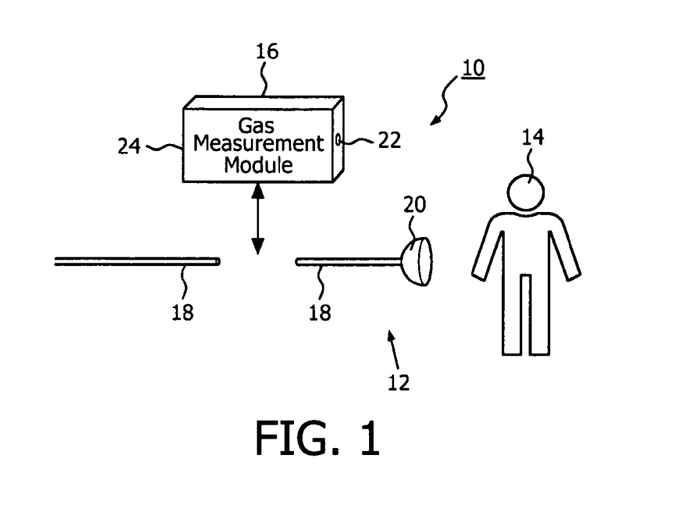
FIG. 1 illustrates a system configured to analyze the composition of gas with in a respiratory circuit, according to one or more embodiments of the invention.

FIG. 1 illustrates a system 10 configured to analyze the composition of gas within a respiratory circuit 12 from which a subject 14 may receive ventilation therapy. In one embodiment, the respiratory circuit 12 is connected at one end to a pressure generator configured to generate a pressurized flow of breathable gas for delivery to the airway of subject 14 through respiratory circuit 12. However, this is not intended to be limiting. In one embodiment, system 10 includes a gas measurement module 16.

The respiratory circuit 12 includes a circuit conduit 18 and a subject interface appliance 20. In a number of different therapeutic scenarios, an airway of subject 14 is engaged to place respiratory circuit 12 in fluid communication with the airway of subject 14. The airway of subject 14 is engaged, and placed in fluid communication with respiratory circuit 12, by subject interface appliance 20. The subject interface appliance 20 may engage one or more orifices of the airway of subject 14 in a sealed or unsealed manner. Some examples of subject interface appliance 20 may include, for example, an endotracheal tube, a nasal cannula, a tracheotomy tube, a nasal mask, a nasal/oral mask, a full face mask, a total face mask, a partial rebreathing mask, or other interface appliances that communicate a flow of gas with an airway of a subject. The present invention is not limited to these examples, and contemplates implementation of any subject interface.

The circuit conduit 18 is configured to convey gas toward and away from subject interface appliance 20. By way of non-limiting example, circuit conduit 18 may include a flexible conduit. For the purposes of this disclosure, circuit conduit 18 is not necessarily limited to a tubular member that conveys pressurized gas flows to and/or from subject interface appliance 20. The circuit conduit 18 may include any hollow body, container, and/or chamber placed in fluid communication with the airway of subject 14 by subject interface appliance 20. For example, the circuit conduit 18 referred to herein may be formed as a chamber located on the actual subject interface appliance 20. This chamber may be in fluid communication with a gas source, and/or with ambient atmosphere.

The gas measurement module 16 is configured to analyze the composition of gas within respiratory circuit 12. As such, gas measurement module 16 is configured to be placed in communication with circuit conduit 18. This may include insertion of gas measurement module 16 into circuit conduit 18. This insertion may be selectively removable, and/or substantially permanent. In one embodiment, respiratory circuit 12 includes a dock in circuit conduit 18 configured to removably receive gas measurement module 16 therein. The gas measurement module 16 forms a chamber therein having a first opening 22 and a second opening 24 disposed on gas measurement module 16 such that if gas measurement module 16 is inserted into circuit conduit 18, gas is transported to and/or from the airway of subject 14 through a flow path between first opening 22 and second opening 24 formed by the chamber. In some implementations, the chamber is formed as a sidestream chamber (rather than a mainstream chamber). In these implementations, gas passing through gas measurement module 16 between first opening and second opening 24 is drawn off into the sidestream chamber for analysis.

The gas measurement module 16 carries optical and/or electronic components that facilitate analysis of the composition of the gas within the chamber formed by gas measurement module 16. These components may form, for instance, a scanning spectrometer. In order to facilitate the use of gas measurement module 16 in therapeutic settings, the optical and/or electronic components of gas measurement module 16 that facilitate composition analysis are configured to minimize the form factor of gas measurement module 16. For example, if gas measurement module 16 is too bulky and/or awkward, then implementation may be difficult (e.g., susceptible to inadvertent disconnection and/or breakage), uncomfortable for subject 14, and/or have other draw backs. Other design considerations for the measurement module 16 include power usage/efficiency, heat generated through operation, cost of materials and/or manufacture, precision/accuracy in measurement gas composition, and/or other considerations.

Figure 2:
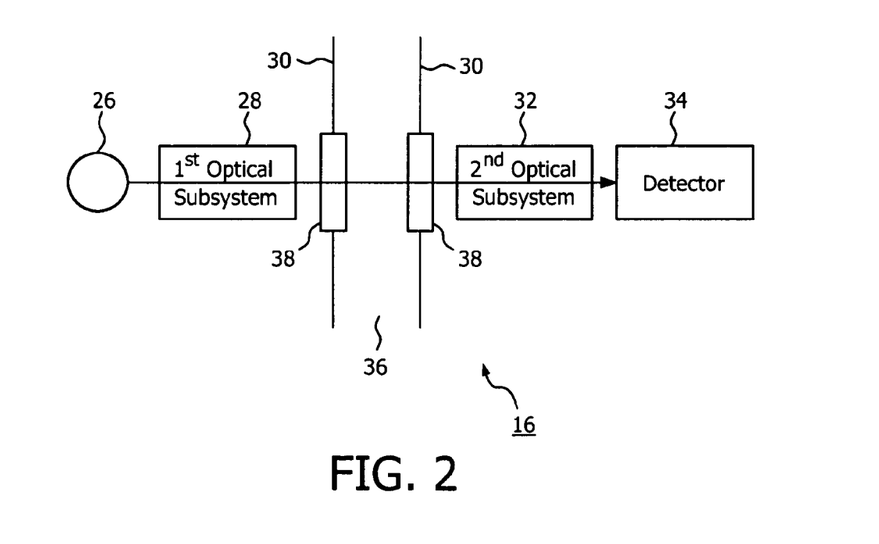
FIG. 2 illustrates a gas measurement module, in accordance with one or more embodiments of the invention.

FIG. 2 illustrates one embodiment of gas measurement module 16. In the embodiment of gas measurement module 16 shown in FIG. 2, gas measurement module 16 includes a source 26, a first optical subsystem 28, an airway adapter 30, a second optical subsystem 32, one or more photosensitive detectors 34, and/or other components.

The source 26 is configured to emit electromagnetic radiation in the infrared spectrum. Source 26 includes an emitter and a lens. The emitter is the body from which electromagnetic radiation emanates, and the lens is generally provided integrally with the emitter. For example, the lens may provide mechanical protection for the emitter, may isolate the emitter from atmosphere, and/or may otherwise be provided integrally with the emitter. In one embodiment, the electromagnetic radiation includes electromagnetic radiation in a first wavelength band related to carbon dioxide or nitrous oxide (e.g., at about 4.25 or about 4.55 microns, respectively), a second wavelength band that provides a reference at 3.7 microns, and/or other wavelength bands. The second wavelength band may provided at a wavelength for which there is little to no absorption by gases within gas measurement module 16.

The first optical subsystem 28 is configured to process the electromagnetic radiation emitted by source 26. Generally, the size and/or shape of source 26 and/or a lens associated with source 26 cause the electromagnetic radiation generated by source 26 to expand as it propagates away from source 26.

The first optical subsystem 28 may include one or more optical elements configured to reduce beam expansion (e.g., one or more elements that collimate electromagnetic radiation).

The airway adapter 30 is configured to be coupled with a respiratory circuit (e.g., respiratory circuit 12 in FIG. 1). The airway adapter 30 further forms a chamber 36 between first opening 22 and second opening 24, within which gas is received from the respiratory circuit for measurement by gas measurement module 16. As can be seen in FIG. 2, on each side of the flow path formed through airway adapter 30 by chamber 36 a window 38 is formed. Each of windows 38 is formed from a material that is optically transparent (or at least translucent) to infrared electromagnetic radiation. For example, windows 38 may be formed from silicon, germanium, sapphire, and/or other materials. The electromagnetic radiation emitted by source 26 and processed by first optical subsystem 28 is directed through chamber 36 via windows 38.

The second optical subsystem 32 is configured to process the electromagnetic radiation that has passed through the flow path formed by chamber 36. For example, in one embodiment, second optical subsystem 32 includes one or more optical elements configured to focus the electromagnetic radiation received through chamber 36 onto photosensitive detectors 34.

The photosensitive detectors 34 are configured to generate output signals conveying information related to one or more parameters of the electromagnetic radiation that becomes incident thereon. The one or more parameters may include, for example, intensity as a function of wavelength, and/or other parameters.

In one embodiment, one or both of first optical subsystem 28 and/or second optical subsystem 32 include one or more optical components configured to spatially separate the electromagnetic radiation emitted by source 26 by wavelength. This separation may enable photosensitive detector 34 to generate output signals conveying information related to intensity as a function of wavelength.

In conventional gas measurement systems, attention may be paid to overall form factor, power usage/efficiency, heat generated through operation, cost of materials and/or manufacture, and/or precision/accuracy in measurement gas composition. In such systems, optical subsystems similar to first optical subsystem 28 and/or second optical subsystem 32 that collimate and/or focus electromagnetic radiation are provided. While it may be appreciated that such optical elements may increase the bulk and cost of conventional systems, it has generally been held that the increased precision/accuracy provided by these optical elements outweighs the bulk and/or cost that they add.

In the embodiments of gas measurement module 16 shown and described hereafter, electromagnetic radiation is processed to provide information about the composition of gas within chamber 36 without the use of optical elements that collimate or focus electromagnetic radiation. Instead of processing the radiation to collimate and/or focus the electromagnetic radiation, attention is paid in these embodiments to shortening the optical path between source 26 and photosensitive detector 34. By way of non-limiting example, the optical path length may be kept below about 19 mm (from the emitter). Further, in the embodiments described below, a single photosensitive detector 34 is used to detect the electromagnetic radiation. This may enhance functionality over embodiments that implement two or more detectors, since the single photosensitive detector 34 is self-referencing.

Shortening the optical path between source 26 and photosensitive detector 34 may overcome some of the degradation to precision/accuracy caused by beam expansion in the electromagnetic radiation emitted from source 26. Further, it has been determined that another factor tending to degrade the precision/accuracy of gas measurement module 16 in measuring the composition of gas within chamber 36 is "ambient path length." As used herein, the term "ambient path length" refers to the length of the optical path between source 26 and photosensitive detector 34 for which electromagnetic radiation is exposed to ambient atmosphere (e.g., not within chamber 36). In order to shorten the overall path length in the embodiments discussed below, the ambient path length is shortened. The precision/accuracy gained by this shortening of the ambient path length may at least compensate for any precision/accuracy lost by not collimating and/or focusing electromagnetic radiation within gas measurement module 16. By way of non-limiting example, the "ambient path length" may be kept below about 4.5 mm.

It will be appreciated that there are other techniques available to reduce the exposure of electromagnetic radiation to ambient gases outside of chamber 36. For example, the interior of gas measurement module 16 may be held under vacuum, filled with gas(es) that do not absorb electromagnetic radiation in the wavelengths of interest, and/or formed from an optically transmissive material that keeps ambient atmosphere out of the optical path (e.g., filled with a silicon or sapphire material). However, these alternative solutions may substantially increase the cost of the materials and/or manufacture of gas measurement module 16.

Figure 3:
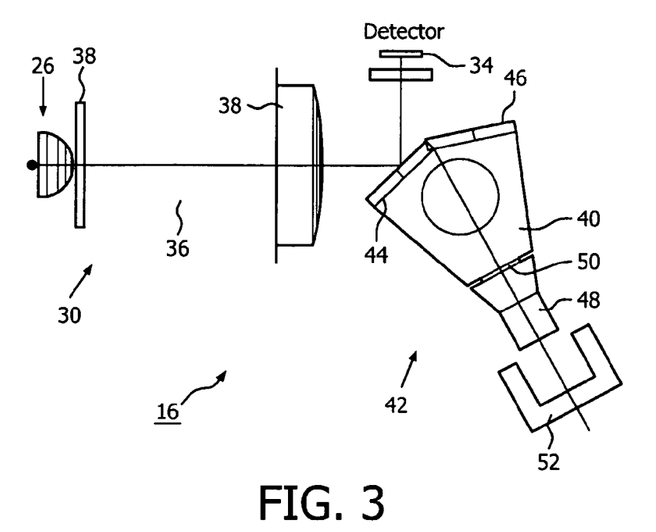
FIG. 3 illustrates a gas measurement module, in accordance with one or more embodiments of the invention.

FIG. 3 illustrates an embodiment of gas measurement module 16 that includes source 26, airway adapter 30, photosensitive detector 34, a filter member 40, an actuator 42, and/or other components. The source 26 is positioned on one side of airway adapter 30 relatively close to window 38. In one embodiment, the emitter within source 26 is less than about 2.74 mm away from window 38. The air distance between the lens of source 26 and window 38 may be less than about 1.2 mm. On an opposite side of airway adapter 30, photosensitive detector 34, filter member 40, and actuator 42 are disposed.

The filter member 40 includes a plurality of filter elements. Specifically, in the embodiment shown in FIG. 3, filter member 40 includes a first filter element 44 and a second filter element 46. The first filter element 44 is configured to filter electromagnetic radiation within a first wavelength band and second filter element 46 is configured to filter electromagnetic radiation within a second wavelength band. This means that first filter element 44 selectively blocks or directs electromagnetic radiation away from the optical path that is not in the first wavelength band and second filter element 46 selectively blocks or directs electromagnetic radiation away from the optical path that is not in the second wavelength band. In one embodiment, the first wavelength band is related to carbon dioxide or nitrous oxide (e.g., at about 4.25 or about 4.55 microns, respectively), and the second wavelength band is a reference. In the embodiment shown in FIG. 3, first filter element 44 and second filter element 46 are reflective filter elements.

This illustration and description of filter member 40 as including only first filter element 44 and second filter element 46 is not intended to limiting. In one embodiment, filter member 40 includes one or more additional filter elements. For example, filter member 40 may include a third filter element configured to filter electromagnetic radiation in a third wavelength band.

The filter member 40 is configured to carry first filter element 44 and second filter element 46 on a side of filter member 40 that faces toward window 38. The filter member 40 is configured to be movable between a plurality of different positions. At each of the positions, one of the filter elements included in filter member 40 (e.g., first filter element 44 or second filter element 46) is disposed in the optical path to such that electromagnetic radiation from source 26 is filtered by the filter element in the optical path before becoming incident on photosensitive detector 34. In the embodiment shown in FIG. 3, filter member 40 is rotatable about an axis of rotation between a first position (as shown) at which first filter element 44 is disposed in the optical path, and a second position at which second filter element 46 is disposed in the optical path. By oscillating filter member 40 back and forth between the first position and the second position, gas measurement module 16 provides electromagnetic radiation to photosensitive detector 34 in both the first wavelength band and the second wavelength band. In one embodiment, this oscillation is periodic according to a predetermined period and/or frequency.

The amount of rotation between the first position and the second position is a function of, among other things, the size of first filter element 44 and second filter element 46, the spatial distance between first filter element 44 and second filter element 46, the radial position(s) of first filter element 44 and second filter element 46, and/or an angle between the surfaces of first filter element 44 and second filter element 46.

The actuator 42 is configured to actuate filter member 40 between the positions corresponding to the filter elements carried by filter member 40. For example, actuator 42 actuates filter member 40 between the first position and the second position. In one embodiment, actuator 42 includes a taut band scanner. The taut band scanner may include a permanent magnet 48, a taut band 50, and a stator 52. The manner in which the taut band scanner works to actuate filter member 40 is described, for instance, in U.S. Pat. No. 7,605,370, issued Oct. 20, 2009, entitled "MICROSPECTROMETER GAS ANALYZER," and hereby incorporated into this disclosure in its entirety.

As actuator 42 actuates filter member 40 to move between the positions corresponding to the filter elements it carries, photosensitive detector 34 generates an output signal conveying information about the intensity of electromagnetic radiation becoming incident thereon. Inasmuch as the position of filter member 40 and/or actuator 42 is known, this output signal provides information about the intensity of the electromagnetic radiation as a function of wavelength. This can be used to determine information about the composition of gas within airway adapter 30.

In one embodiment, filter member 40 and photosensitive detector 34 are configured within gas measurement module 16 to reduce the ambient path length between window 38 and photosensitive detector 34. For example, the ambient path length between window 38 and photosensitive detector 34 may be maintained at less than about 3.1 mm.

It will be appreciated that the use of filters to selectively provide wavelength bands of electromagnetic radiation to photosensitive detector 34 for detection may reduce the power efficiency of gas measurement module 16 with respect to embodiments in which a plurality of photosensitive detectors 34 are implemented. However, by shortening the path length of the system, the loss of power associated with only providing a portion of the electromagnetic radiation to photosensitive detector 34 may be mitigated.

Figure 4:
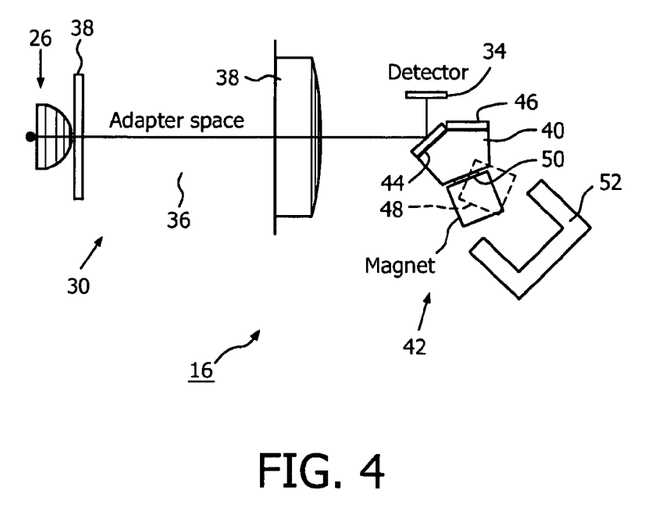
FIG. 4 illustrates a gas measurement module, in accordance with one or more embodiments of the invention.

FIG. 4 illustrates another embodiment of gas measurement module 16. In the illustration of FIG. 4, components have been labeled in common with components previously illustrated providing corresponding functionality. As can be seen in FIG. 4, this embodiment includes source 26, airway adapter 30, photosensitive detector 34, filter member 40, actuator 42, and/or other components. FIG. 4 provides an illustration of, among other things, the manner in which radial distance between the axis of rotation of filter member 40 and the filter elements (e.g., first filter element 44 and second filter element 46) impacts the amount by which filter member 40 must be rotated between the positions corresponding to the filter elements. Because this radial distance is shorter in the embodiment shown in FIG. 4 than in the embodiment shown in FIG. 3, filter member 40 must be rotated over a larger angle between the first position and the second position. Thus, while reducing the radial distance may provide for a more compact form factor, the increased rotation required to effectively move filter member 40 between the requisite positions may place an increased burden on the other components of gas measurement module 16 (e.g., on actuator 42).

Figure 5:
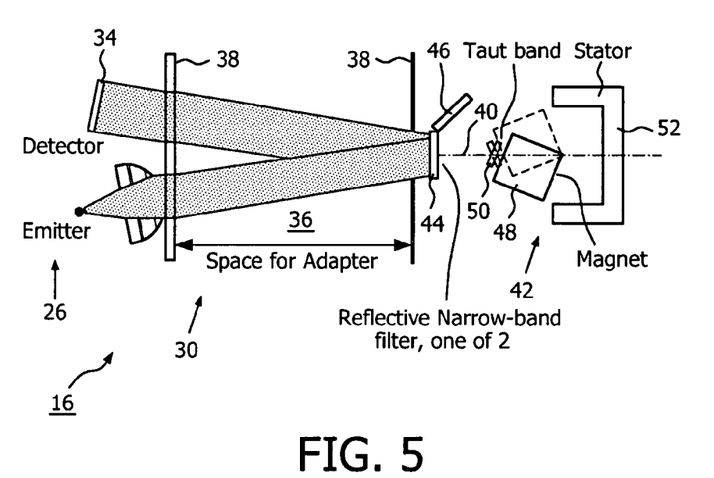
FIG. 5 illustrates a gas measurement module, in accordance with one or more embodiments of the invention.

FIG. 5 illustrates yet another embodiment of gas measurement module 16. In the illustration of FIG. 5, components have been labeled in common with components previously illustrated providing corresponding functionality. In the embodiment shown in FIG. 5, photosensitive detector 34 is positioned on a side of airway adapter 30 opposite from filter member 40. As such, electromagnetic radiation from source 26 passes through chamber 36 to filter member 40, and then is reflected back through chamber 36 to photosensitive detector 34. This may enable reduction of the width of chamber 36 without reducing the path length of the optical path through chamber 36 (as the electromagnetic radiation travels both to and fro through chamber 36). To reduce the ambient path length, the emitter of source 26 may be positioned less than about 2.74 mm from window 38 and/or the lens of source 26 may be less than about 1.2 mm, filter member 40 may be positioned such that when they are disposed in the optical path the filter elements are less than about 2.45 mm from window 38, and/or photosensitive detector 34 may be positioned such that the ambient path length between window 38 and photosensitive detector 34 is less than about 0.4 mm.

Figure 6:
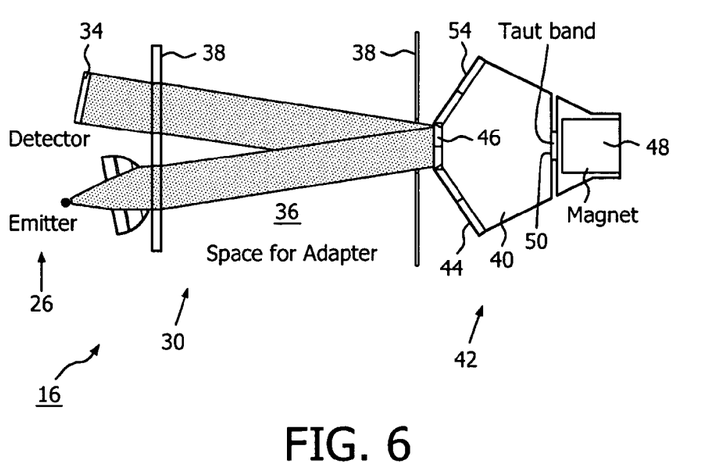
FIG. 6 illustrates a gas measurement module, in accordance with one or more embodiments of the invention.

FIG. 6 illustrates yet another embodiment of gas measurement module 16. In the illustration of FIG. 6, components have been labeled in common with components previously illustrated providing corresponding functionality. In the embodiment shown in FIG. 6, filter member 40 is depicted having a larger radial distance between the axis of rotation of filter member 40 and the filter elements carried by filter member 40 than the embodiment shown in FIG. 6. As was discussed above, this may reduce the angle over which filter member 40 must be rotated to move between the positions corresponding to the filter elements. FIG. 6 further shows filter member 40 including a third filter element 54. The third filter element is configured to filter electromagnetic radiation in a third wavelength band. In the embodiment shown in FIG. 6, actuating filter member 40 between the positions corresponding to the filter elements carried by filter member 40 includes actuating filter member between the first position, the second position, and a third position at which third filter element 54 is disposed in the optical path to filter electromagnetic radiation emitted by source 26 before the electromagnetic radiation becomes incident on photosensitive detector 34.

Figure 7:
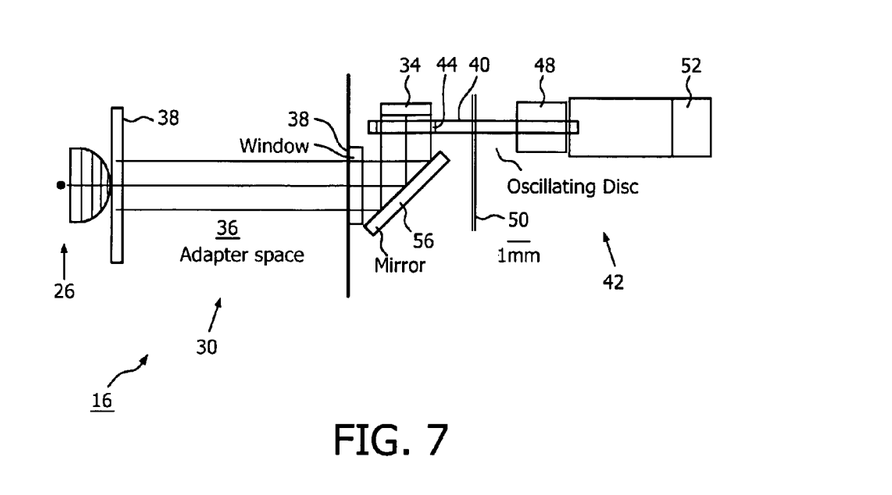
FIG. 7 illustrates a gas measurement module, in accordance with one or more embodiments of the invention.
Figure 8:
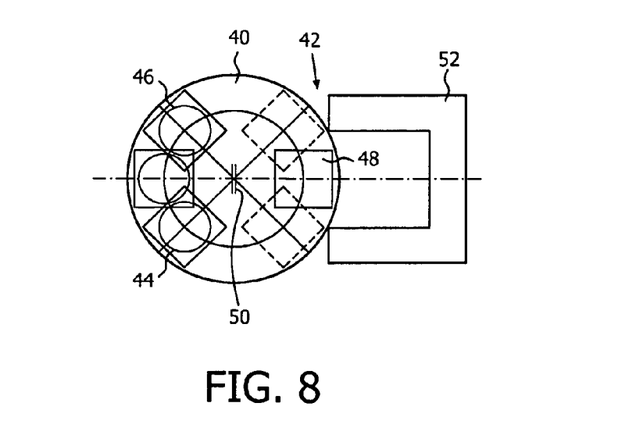
FIG. 8 illustrates a gas measurement module, in accordance with one or more embodiments of the invention.

FIGS. 7 and 8 illustrate still another embodiment of gas measurement module 16. In the illustration of FIGS. 7 and 8, components have been labeled in common with components previously illustrated providing corresponding functionality. In the embodiment shown in FIGS. 7 and 8, filter member 40 is formed generally having a disk-shape, with the filter elements (e.g., first filter element 44 and second filter element 46) provided on the disk. A mirror 56 is configured to bend the optical path toward photosensitive detector 34. The filter member 40 is disposed within gas measurement module 16 such that the optical path intersects filter member 40. The filter member 40 is rotatable about an axis of rotation (e.g., located at taut band 50) by actuator 42. The actuator 42 is configured to rotate filter member 40 about the axis of rotation to positions at which the filter elements carried by filter member 40 are disposed in the optical path to filter the electromagnetic radiation. The ambient path length between window 38 and photosensitive detector 34 may be maintained at about 2.5 mm.

Figure 9:
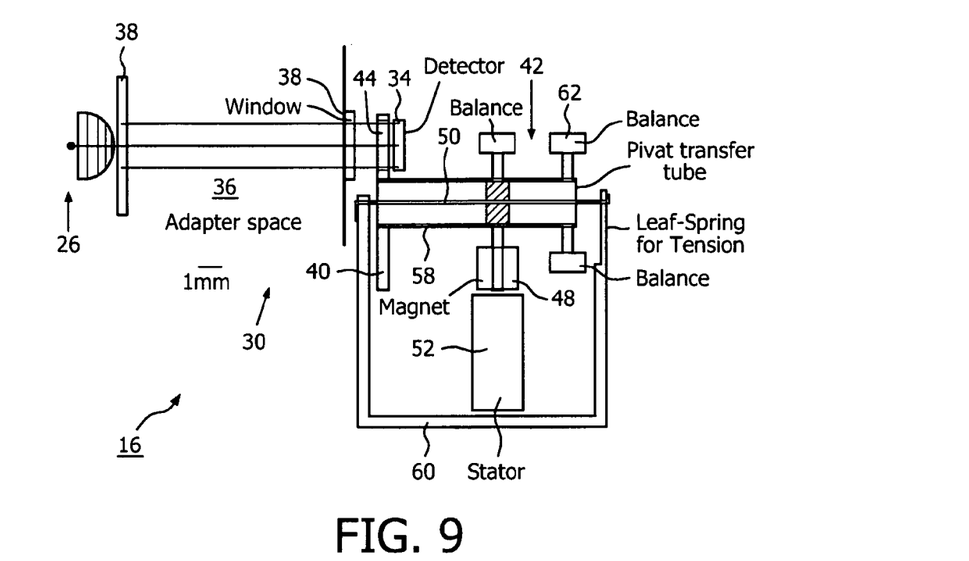
FIG. 9 illustrates a gas measurement module, in accordance with one or more embodiments of the invention.
Figure 10:
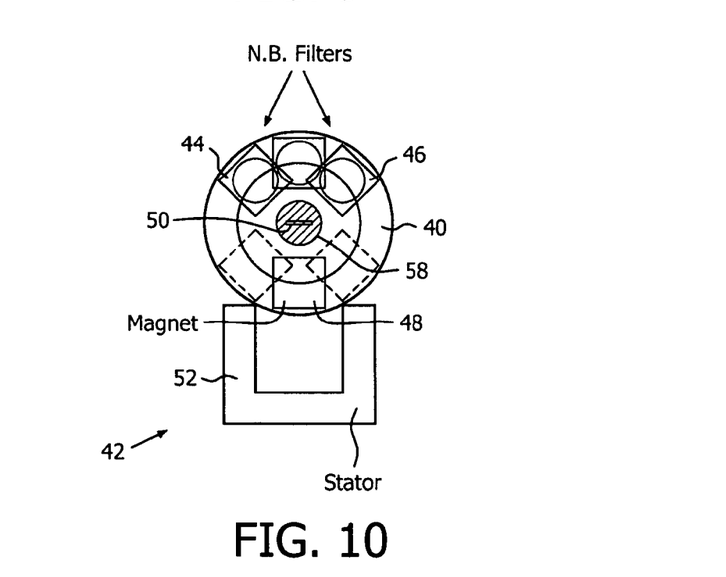
FIG. 10 illustrates a gas measurement module, in accordance with one or more embodiments of the invention.

FIGS. 9 and 10 illustrate a still further embodiment of gas measurement module 16. In the illustration of FIGS. 9 and 10, components have been labeled in common with components previously illustrated providing corresponding functionality. In the embodiment shown in FIGS. 9 and 10, gas measurement module 16 has been modified work with a filter member 40 having a general disk shape with the filter elements carried in the flat of the disk, and without a mirror bending the optical path toward filter member 40 and photosensitive detector 34. In this embodiment, the plane of the disk forming filter member 40 may be generally parallel with (or tangential to) the surface of window 38 closest to filter member 40. The ambient path length between window 38 and photosensitive detector 34 may be maintained at less than about 1.0 mm.

To facilitate rotation of filter member 40 between the positions corresponding to the filter elements, actuator 42 may include a hollow tube 58, a leaf spring 60, a counter balance 62, and/or other components. The hollow tube 58 is attached to filter member 40 at a first end of filter member 40 such that the cross section of hollow tube 58 surrounds the axis of rotation of filter member 40. The taut band 50 runs through hollow tube 58, and is attached at each end to leaf spring 60. The leaf spring 60 has a U-shape, and serves to hold taut band 50 under tension. The permanent magnet 48 is attached to hollow tube 58 along hollow tube 58 away from the first end. On a side of permanent magnet 48 opposite the first end of hollow tube 58, counter balance 62 is attached to hollow tube 58. The counter balance 62 serves to balance the filter member 40/hollow tube 58 member about permanent magnet 48.

Figure 11:
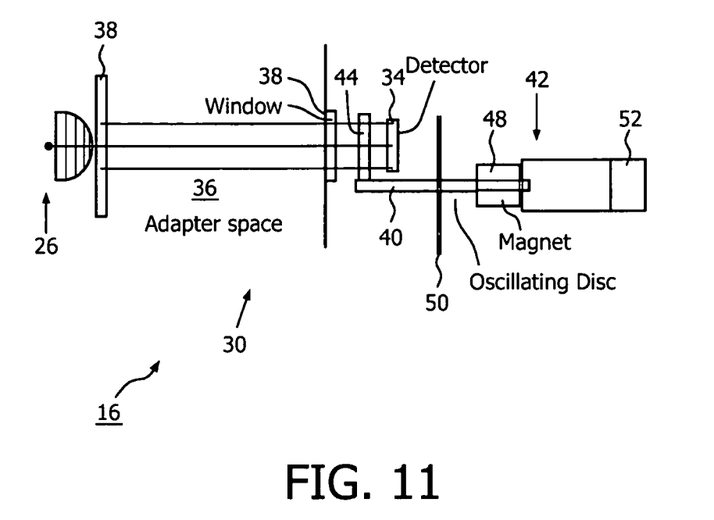
FIG. 11 illustrates a gas measurement module, in accordance with one or more embodiments of the invention.
Figure 12:
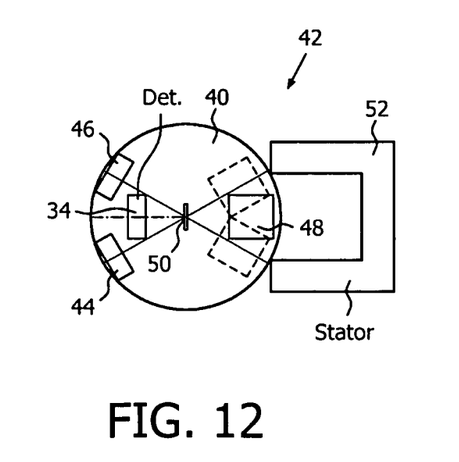
FIG. 12 illustrates a gas measurement module, in accordance with one or more embodiments of the invention.

FIGS. 11 and 12 illustrate yet another embodiment of gas measurement module 16. In the illustration of FIGS. 11 and 12, components have been labeled in common with components previously illustrated providing corresponding functionality. In the embodiment shown in FIGS. 11 and 12, filter member 40 is formed as a disk-shaped member, but the filter elements (e.g., first filter element 44 and second filter element 46) do not lie in the flat of the disk, as was shown in FIGS. 7-10. Instead, the filter elements are disposed to extend from the plane of filter member 40. The disk-shaped filter member 40 rotates about an axis of rotation formed by taut band 50, which runs through the center of filter member 40. In this embodiment, the ambient path length between window 38 and photosensitive detector 34 may be maintained at less than about 1.0 mm.

In the embodiments of gas measurement module 16 illustrated in FIGS. 3-12, filter member 40 is configured such that there is some spatial separation between the positions corresponding to the filter elements. For example, with respect to the first position and the second position, first filter element 44 and second filter element 46 are disposed on filter member 40 such that the rotationally displacing filter member 40 between the first position and the second position requires filter member 40 to be swept over an angle at which neither first filter element 44 nor second filter element 46 is positioned to direct electromagnetic radiation toward photosensitive detector 34. This configuration of filter member 40 with "intermediate" positions between the positions that correspond to the filter elements may reduce optical interference (e.g., caused by photosensitive detector 34 receiving some electromagnetic radiation that has been filtered by first filter element 44 and some electromagnetic radiation that has been filtered by second filter element 46). However, this configuration may increase the range of motion required by the filter member 40/actuator 42 system, and/or may result in the generation of heat (caused by electromagnetic radiation that becomes incident on filter member 40 in between positions) within gas measurement module 16. Requiring actuator 42 to actuate filter member 40 over a larger range of motion may increase the strain on actuator 42, may increase the amount of energy consumed by actuator 42, and/or may present other drawbacks.

In one embodiment, to reduce the amount of spatial separation required between the positions of the filter member 40 corresponding to the filter elements carried by filter member 40, electromagnetic radiation may be kept from coming incident on filter member 40 when filter member 40 is in between positions. For example, as filter member 40 is being actuated between the first position and the second position, electromagnetic radiation emitted by source 26 may be blocked from becoming incident on filter member 40. This blockage may be accomplished by a gate that selectively blocks the optical path. The gate may be positioned, for example, between source 26 and window 38 or between window 38 and filter member 40.

In one embodiment, rather than (or in combination with) the blocking of electromagnetic radiation, the output signal of photosensitive detector 34 is selectively blocked or discarded while the filter member 40 is between the first position and the section position. This gating of the output signal of photosensitive detector 34 may be done using a switch that selectively couples photosensitive detector 34 to a processor.

In one embodiment, instead of (or in conjunction with) the gating of the output signal of photosensitive detector and/or the blocking of electromagnetic radiation, source 26 is controlled to emit the electromagnetic radiation in pulses that are coordinated with filter member 40 being positioned at a position corresponding to a filter element. For example, when filter member 40 is positioned at the first position a pulse of electromagnetic radiation may be emitted by source 26. As filter member 40 is actuated from the first position to the second position, source 26 may not emit electromagnetic radiation. When filter member 40 reaches the second position, source 26 may emit another pulse of electromagnetic radiation, and so on. The coordination between filter member 40 and source 26 may be accomplished by one or more controllers that control source 26 and/or actuator 42. The use of pulsed electromagnetic radiation that coincides with the actuation of filter member 40 may reduce heat generation within gas measurement module 16, may enhance the efficiency of gas measurement module 16 in generating electromagnetic radiation, and/or may provide other enhancements.

It will be appreciated that the illustration and description herein of embodiments in which filter member 40 is positioned on a side of airway adapter 30 opposite from source 26 is not intended to be limiting. The scope of this disclosure encompasses arrangements of gas measurement module 16 in which filter member 40 is positioned to filter electromagnetic radiation emitted by source 26 prior to the electromagnetic radiation being directed through airway adapter 30.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A gas measurement module configured to be inserted into a respiratory circuit that is in fluid communication with an airway of a subject, the gas measurement module comprising:
   a chamber having a first opening and a second opening, wherein the chamber is configured to form a flow path between the first opening and the second opening such that if the gas measurement module is inserted into the respiratory circuit, gas from the airway of the subject is transported through the flow path;
   an infrared source configured to emit infrared electromagnetic radiation along an optical path that passes through the flow path formed by the chamber;
   a movable filter member including a first filter element configured to filter electromagnetic radiation in a first wavelength band and a second filter element configured to filter electromagnetic radiation in a second wavelength band;
   a photosensitive detector held at a fixed position along the optical path to receive infrared electromagnetic radiation that has been filtered by the filter member and has passed through the flow path formed by the chamber, and to generate output signals that convey information related to one or more parameters of the received infrared electromagnetic radiation; and
   an actuator configured to actuate the filter member between a first position and a second position, wherein at the first position the first filter element is positioned in the optical path, and wherein at the second position the second filter element is positioned in the optical path, wherein one or more of
   (i) the electromagnetic energy is blocked from becoming incident on the filter member as filter member is being actuated between the first position and the second position, via a gate positioned between (i)(a) the infrared source and the first opening and (i)(b) the second opening and the filter member to selectively block the optical path,
   (ii) the output signal of the photosensitive detector is disconnected from a processor in response to the filter member being actuated between the first position and the second position, via a switch that selectively couples the output signal of the photosensitive detector to the processor, and
   (iii) the infrared source is controlled to emit the electromagnetic radiation in pulses that are coordinated with the filter member being positioned at a position corresponding to a filter element, via one or more controllers that control one or more of the infrared source and the actuator.

2. The gas measurement module of claim 1, wherein the filter member further includes a third filter element configured to filter electromagnetic radiation in a third wavelength band, wherein the actuator is further configured to actuate the filter member to the first position, the second position and a third position, and wherein at the third position the third filter element is positioned in the optical path.

3. The gas measurement module of claim 1, wherein the length of the optical path from the infrared source to the fixed position of the photosensitive detector is less than about 19 mm.

4. The gas measurement module of claim 1, wherein the filter member is disposed along the optical path downstream from the chamber.

5. The gas measurement module of claim 1, wherein the filter member is rotatable around an axis of rotation, and wherein the first position is a first rotational orientation of the filter member and the second position is a second rotational orientation of the filter member.

6. A method of analyzing gas within a gas measurement module configured to be inserted into a respiratory circuit that is in fluid communication with an airway of a subject, the method comprising:
   emitting, via an infrared source, infrared electromagnetic radiation along an optical path that passes through a flow path formed by the gas measurement module within which gas from the airway of the subject flows;
   actuating, via an actuator, a filter member between a first position and a second position, wherein at the first position a first filter element of the filter member is disposed in the optical path and at the second position a second filter element of the filter member is disposed in the optical path, and wherein the first filter element is configured to filter electromagnetic radiation in a first wavelength range and the second filter element is configured to filter electromagnetic radiation in a second wavelength range;
   receiving, via a photosensitive detector, electromagnetic radiation along the optical path that has been filtered by the filter member; and
   generating, via the photosensitive detector, output signals that convey information related to one or more parameters of the received infrared electromagnetic radiation, wherein one or more of
   (i) the electromagnetic energy is blocked from becoming incident on the filter member as filter member is being actuated between the first position and the second position, via a gate positioned between (i)(a) the infrared source and a first opening of a chamber of the gas measurement module and (i)(b) a second opening of the chamber and the filter member to selectively block the optical path,
   (ii) the output signals of the photosensitive detector are disconnected from a processor in response to the filter member being actuated between the first position and the second position, via a switch that selectively couples the output signals of the photosensitive detector to the processor, and
   (iii) the infrared source is controlled to emit the electromagnetic radiation in pulses that are coordinated with the filter member being positioned at a position corresponding to a filter element, via one or more controllers that control one or more of the infrared source and the actuator.

7. The method of claim 6, wherein actuating the filter member further comprises actuating the filter member to a third position at which a third filter element of the filter member is disposed in the optical path, and wherein the third element is configured to filter electromagnetic radiation in a third wavelength range.

8. The method of claim 6, wherein the length of the optical path is less than about 19 mm.

9. The method of claim 6, wherein the filter member is disposed along the optical path downstream from the flow path.

10. The method of claim 6, wherein actuating the filter member between the first position and the second position comprises rotating the filter member between a first rotational orientation of the filter member that corresponds to the first position and a second rotational orientation of the filter member that corresponds to the second position.

11. A system configured to analyze gas within a chamber, wherein the system configured to be inserted into a respiratory circuit that is in fluid communication with an airway of a subject, the system comprising:

means for emitting infrared electromagnetic radiation along an optical path that passes through a flow path within which gas from the airway of the subject flows;

means for filtering electromagnetic radiation disposed along the optical path, wherein the means for filtering comprise first means for filtering electromagnetic radiation in a first wavelength range and second means for filtering electromagnetic radiation in a second wavelength range;

means for actuating the means for filtering between a first position and a second position, wherein at the first position the first means for filtering filter electromagnetic radiation traveling along the optical path and at the second position the second means for filtering filter electromagnetic radiation traveling along the optical path;

means for receiving electromagnetic radiation along the optical path that has been filtered by the means for filtering and generating output signals that convey information related to one or more parameters of the received infrared electromagnetic radiation, wherein one or more of (i) the electromagnetic energy is blocked from becoming incident on the means for filtering as means for filtering is being actuated between the first position and the second position, via a gate positioned between (i)(a) the means for emitting and a first opening in the chamber and (i)(b) a second opening in the chamber and the means for filtering to selectively block the optical path, (ii) the output signals of the means for receiving and generating are disconnected from a processor in response to the means for filtering being actuated between the first position and the second position, via a switch that selectively couples the output signals of the means for receiving and generating to the processor, and (iii) the means for emitting is controlled to emit the electromagnetic radiation in pulses that are coordinated, with the means for filtering being, positioned at a position corresponding to a filter element, via one or more controllers that control one or more of the means for emitting and the means for actuating.

12. The system of claim 11, wherein means for filtering further comprise a third means for filtering electromagnetic radiation in a third wavelength range, and wherein the means for actuating the means for filtering are further configured to actuate the means for filtering to a third position at which the third means for filtering filter electromagnetic radiation traveling along the optical path.

13. The system of claim 11, wherein the length of the optical path is less than about 19 mm.

14. The system of claim 11, wherein the means for filtering are disposed along the optical path downstream from the flow path.

15. The system of claim 11, wherein the means for actuating the means for filtering between the first position and the second position comprises rotating the means for filtering between a first rotational orientation that corresponds to the first position and a second rotational orientation that corresponds to the second position.

* * * * *